United States Patent
Kruse et al.

(10) Patent No.: US 9,804,004 B1
(45) Date of Patent: Oct. 31, 2017

(54) FLUID QUALITY SENSOR AND COVER ASSEMBLY

(71) Applicant: DEERE & COMPANY, Moline, IL (US)

(72) Inventors: Ryan J. Kruse, Asbury, IA (US); Michael F. Flanagan, Bettendorf, IA (US); Jonathan R. Copeland, Peosta, IA (US); Francis J. Lahey, Sherrill, IA (US)

(73) Assignee: Deere & Company, Moline, IL (US)

( * ) Notice: Subject to any disclaimer, the term of this patent is extended or adjusted under 35 U.S.C. 154(b) by 20 days.

(21) Appl. No.: 15/153,791

(22) Filed: May 13, 2016

(51) Int. Cl.
*G01D 11/24* (2006.01)
*G01M 15/10* (2006.01)

(52) U.S. Cl.
CPC ......... *G01D 11/245* (2013.01); *G01M 15/102* (2013.01)

(58) Field of Classification Search
CPC ....................................................... G01N 29/02
USPC ............................................... 73/19.1, 19.03
See application file for complete search history.

(56) References Cited

U.S. PATENT DOCUMENTS

| | | | |
|---|---|---|---|
| 4,079,623 A | 3/1978 | Erwin, Jr. | |
| 7,118,206 B1 | 10/2006 | Stockwell et al. | |
| 9,038,374 B2 | 5/2015 | Bruck et al. | |
| 9,089,791 B2 | 7/2015 | Myer et al. | |
| 9,248,390 B2 | 2/2016 | Hudgens et al. | |
| 9,376,950 B2 | 6/2016 | Ogawa et al. | |
| 2003/0181794 A1 | 9/2003 | Rini et al. | |
| 2011/0138790 A1 | 6/2011 | Radillo et al. | |
| 2011/0166802 A1 | 7/2011 | Kong et al. | |
| 2011/0228641 A1 | 9/2011 | Niemann | |
| 2012/0181261 A1 | 7/2012 | Bruck et al. | |
| 2014/0334983 A1* | 11/2014 | Yang ....................... | F01N 11/00 422/119 |
| 2015/0089996 A1* | 4/2015 | Reimer .................. | G01N 29/02 73/19.03 |
| 2015/0153213 A1* | 6/2015 | Kopansky ............... | G01F 23/02 250/577 |
| 2015/0196862 A1 | 7/2015 | Cassidy et al. | |
| 2015/0218990 A1 | 8/2015 | Hudgens | |
| 2015/0240683 A1 | 8/2015 | Hudgens et al. | |
| 2016/0018363 A1* | 1/2016 | Reimer .................. | G01N 29/02 73/19.03 |

FOREIGN PATENT DOCUMENTS

| | | |
|---|---|---|
| JP | 63-250559 A | 10/1988 |
| JP | 2005299441 | 10/2005 |

\* cited by examiner

*Primary Examiner* — Lisa Caputo
*Assistant Examiner* — Jamel Williams
(74) *Attorney, Agent, or Firm* — Taft Stettinius & Hollister LLP; Stephen F. Rost

(57) ABSTRACT

A sensor assembly is provided for detecting a concentration of a fluid. The sensor assembly includes a sensing unit and a cover assembly. The sensing unit includes a transmitter configured to transmit a signal into a sensing volume and a receiver configured to receive the signal after the signal passes through a portion of the sensing volume. The cover assembly at least partially encloses the sensing volume and is substantially impermeable to a gas portion of the fluid. The cover assembly includes apertures defined therein which are permeable to the gas portion of the fluid. A first plurality of apertures are defined along a top surface of the cover assembly.

20 Claims, 5 Drawing Sheets

FLUID QUALITY SENSOR AND COVER ASSEMBLY

FIELD OF THE DISCLOSURE

The present disclosure relates to a sensor assembly, and in particular to a sensor and cover assembly for detecting a fluid quality.

BACKGROUND OF THE DISCLOSURE

Exhaust treatment fluids such as diesel exhaust fluid (DEF) may be used in a vehicle's exhaust after treatment system. The fluid is stored in a tank or container on a vehicle, and is injected into an exhaust stream to breakdown harmful pollutants such as mono-nitrogen oxides (NOx) into harmless by-products such as ammonia and carbon dioxide. The storage tank may include one or more sensors for determining a temperature of the fluid level, a fluid level in the tank, and a concentration or quality of the fluid in the tank.

During vehicle or machine operation, the fluid inside the tank may move around particularly as the vehicle or machine travels over different terrains. When the fluid level inside the tank is low, it may splash or slosh resulting in air or gaseous bubbles forming in the fluid. The air or gaseous bubbles can interfere with the one or more sensors inside the tank and distort measurements or readings taken by the one or more sensors.

SUMMARY

In one embodiment of the present disclosure, a sensor assembly is provided for detecting a concentration of a fluid. The sensor assembly includes a sensing unit including a transmitter configured to transmit a signal into a sensing volume and a receiver configured to receive the signal after the signal passes through a portion of the sensing volume; a cover assembly at least partially enclosing the sensing volume and being substantially impermeable to a gas portion of the fluid, the cover assembly including apertures defined therein which are permeable to the gas portion of the fluid; wherein, a first plurality of apertures are defined along a top surface of the cover assembly.

In one example of this embodiment, the signal is sonic. In a second example, the cover assembly includes a bottom surface and a second plurality of apertures are defined in the bottom surface. In a third example, the top surface includes a curved cross-section forming an arc, the arc having a first end and a second end, where the top surface defines an uppermost portion positioned at a location at or between the first and second ends of the arc. In a fourth example, the apertures are positioned at a location in the cover assembly nearest the transmitter. In a fifth example, the apertures are positioned at a location in the cover assembly nearest the receiver. In a sixth example, the cover assembly is oriented with respect to the sensing unit and sensing volume such that the first plurality of apertures are positioned at or near a location in the top surface of the cover assembly where the gas portion of the fluid aggregates.

In another embodiment of the present disclosure, a sensor assembly is provided for detecting a quality of fluid inside a diesel exhaust fluid tank assembly. The sensor assembly includes a sensor including a first plate for transmitting a sonic signal through a sensing volume, a second plate spaced from the first plate for receiving the sonic signal as the sonic signal passes through at least a portion of the sensing volume, and a plurality of support members spaced from one another and coupled between the first and second plates; a cover assembly including an outer wall at least partially enclosing the sensor, the cover assembly being impermeable to a gas portion of the fluid except for openings defined in the outer wall of the cover assembly which are permeable to the gas portion of the fluid to allow the gas portion to escape from the sensing volume therethrough; a baffle disposed around the cover assembly and sensor; wherein, a first plurality of openings is defined in a top portion of the outer wall of the cover assembly; further wherein, a first space is defined between the cover assembly and the first plate and a second space is defined between the cover assembly and the second plate, the first space and the second space being permeable to the gas portion of the fluid.

In one example of this embodiment, the cover assembly floats relative to the sensor. In a second example, a bottom portion of the outer wall of the cover assembly is open and does not enclose the sensing volume. In a third example, the cover assembly is coupled to the first plate, the second plate or one of the plurality of support members. In a fourth example, the first plurality of openings includes one or more longitudinal slots defined in the top portion of the outer wall. In a fifth example, the one or more longitudinal slots are substantially parallel to the plurality of support members; and each of the one or more longitudinal slots is defined in the cover assembly at a location spaced from each of the plurality of support members.

In another example of this embodiment, the outer wall of the cover assembly forms a first curvature and a second curvature, the first curvature positioned at the first space and the second curvature positioned at the second space. In a further example, the outer wall of the cover assembly comprises a first side wall, a second side wall, a top wall, and a bottom wall, the bottom wall coupled to the first side wall and the second side wall; and the top wall, bottom wall, first side wall, and second side wall form a continuous structure that substantially surrounds the sensor. In yet a further example, the baffle is defined about a first axis passing therethrough; and the cover is defined about a second axis passing therethrough; further wherein, the first axis is perpendicular to the second axis.

In a further embodiment of the present disclosure, a diesel exhaust fluid tank assembly for containing a fluid includes a tank defining an interior cavity for holding diesel exhaust fluid; a header assembly coupled to the tank, the header assembly including a fluid level sensor and a temperature sensor coupled thereto; a sensor disposed in the interior cavity of the tank, the sensor including a first plate for transmitting a sonic signal through a sensing volume, a second plate spaced from the first plate for receiving the sonic signal after it passes through at least a portion of the sensing volume, and a plurality of support members spaced from one another and coupled between the first and second plates, wherein the first plate is coupled to the header assembly; a cover assembly at least partially enclosing the sensing volume, the cover assembly including a top wall, a first side wall, and a second side wall, the cover assembly being open at both ends such that a first space is defined between the cover assembly and the first plate and a second space is defined between the cover assembly and the second plate; and a baffle coupled to the header assembly and enclosing the cover assembly and sensor; wherein, the cover assembly is impermeable to a gas portion of the fluid except for openings defined in the cover assembly and the first and second spaces which are permeable to the gas portion.

In one example of this embodiment, the cover assembly includes a first plurality of openings defined in or near the top wall to allow the gas portion of the fluid to escape from the sensing volume through the cover assembly. In a second example, the first plurality of openings includes one or more longitudinal slots, the one or more longitudinal slots are substantially parallel to the plurality of support members, and each of the one or more longitudinal slots is defined in the cover assembly at a location spaced from each of the plurality of support members. In another example, the first plurality of openings are equally spaced from one another and the first and second spaces.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

Corresponding reference numerals are used to indicate corresponding parts throughout the several views.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Government regulations in the United States and elsewhere have mandated certain emission requirements from engine manufacturers. To meet these regulations, engine and other manufacturers are producing after treatment exhaust systems to reduce pollutant gases that exhaust from engines. In some cases, nitrogen oxides (NOx) may be reduced by approximately 80%.

Figure 1:
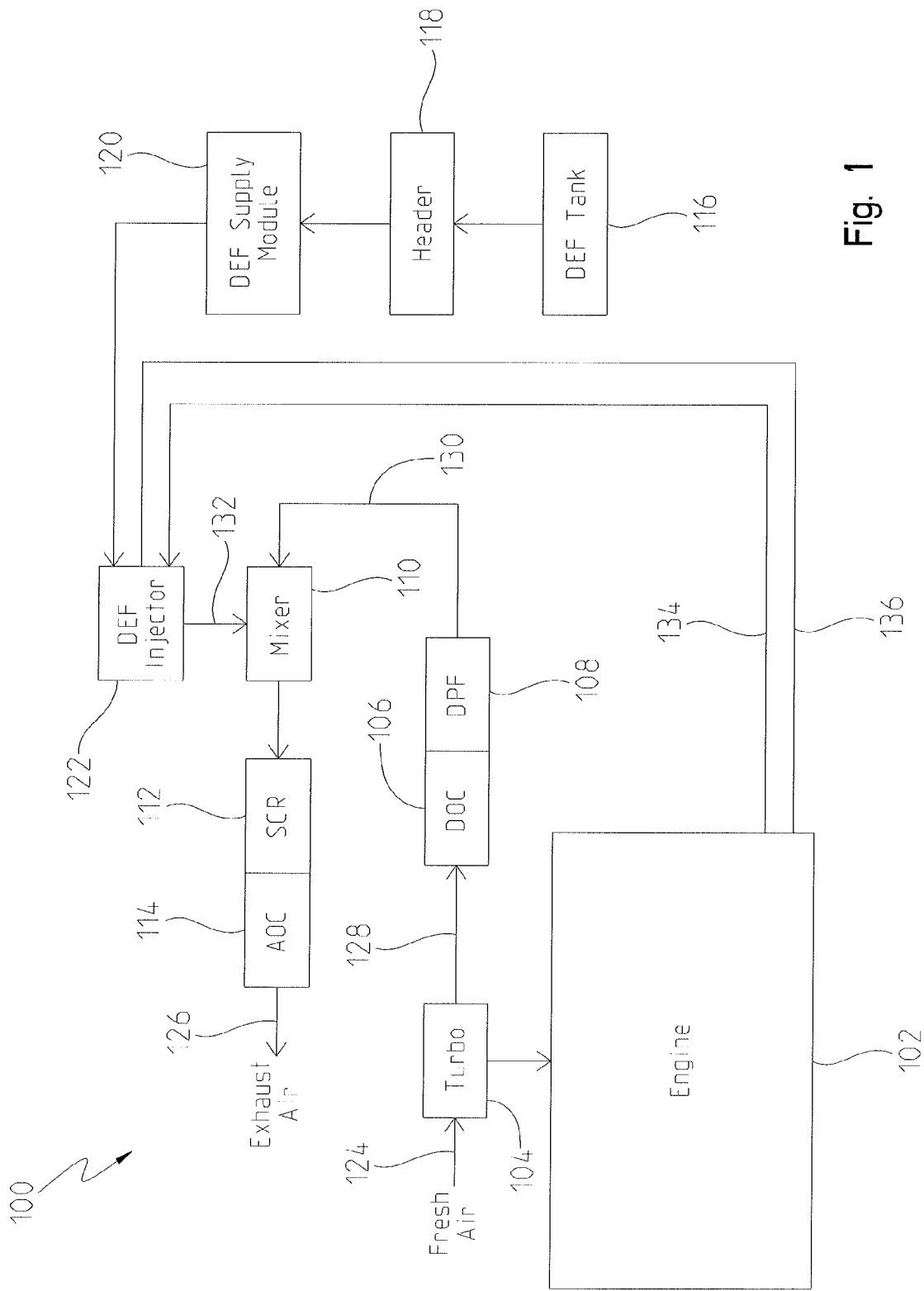
FIG. 1 is a system diagram of an after treatment system including a diesel exhaust fluid tank.

Referring to FIG. 1, a simplified embodiment of an after treatment exhaust system 100 is provided. In this system 100, a diesel engine 102 is shown being fluidly coupled to a turbocharger 104. The engine 102 can be any type of engine for purposes of this disclosure, and the turbocharger 104 may be a variable geometry turbocharger, a series turbocharger, a wastegate turbocharger, or any other known turbocharger. As shown, fresh air 124 can enter the turbocharger 104. Some of the air is compressed and may pass through an intake throttle valve (not shown), an exhaust gas recirculation (EGR) valve, and cooler. Another portion of the air becomes exhaust gases 128 as it exits the turbocharger 104 and enters a catalyzed exhaust filter that contains a diesel oxidation catalysis (DOC) 106 and a diesel particulate filter (DPF) 108. The DOC 106 can react with the exhaust gases 128 to reduce carbon monoxide, hydrocarbons, and some particulate matter. The downstream DPF 108 can force the exhaust gases to flow through porous channel walls, thereby trapping and holding the remaining particulate matter.

Exhaust gases 130 may exit the DPF 108 and enter a mixer 110 assembly as shown in FIG. 1. The mixer 110 may include a plurality of inlets, including the one that is fluidly coupled to the DPF 108. As shown in FIG. 1, the after treatment exhaust system 100 may include a diesel exhaust fluid tank 116 that holds diesel exhaust fluid (DEF). DEF is an aqueous urea solution made with a mixture of urea and deionized water. It may be used as a consumable in selective catalytic reduction (SCR) to reduce NOx concentration in the diesel exhaust gases from diesel engines. The DEF may be stored in the DEF tank 116. A header assembly 118 with a plurality of sensors (not shown) coupled thereto may be disposed within the tank 116. The plurality of sensors (not shown) may include a fluid level sensor for detecting a level of DEF contained within the tank 116, a fluid temperature sensor for detecting a temperature of the DEF, and a fluid concentration or quality sensor for detecting the concentration or qualify of the DEF.

The system 100 may include a DEF supply module 120 for supplying the DEF from the tank 116 to a DEF injector 122. A first coolant line 134 and a second coolant line 136 may also be fluidly coupled between the engine 102 and the injector 122 such that the DEF is injected 132 into the exhaust gases 130 to lower the NOx concentration. The fluid exiting the mixer 110 enters a selective catalytic reduction (SCR) 112 and ammonia oxidation catalyst (AOC) 114 as shown in FIG. 1. Exhaust air or gases 126 exit the AOC and enter the surrounding atmosphere.

The system shown in FIG. 1 and described above is one example of an after treatment exhaust system. Other systems may be used, and the teachings and principles of the present disclosure may apply to any one of these types of systems.

Figure 2:
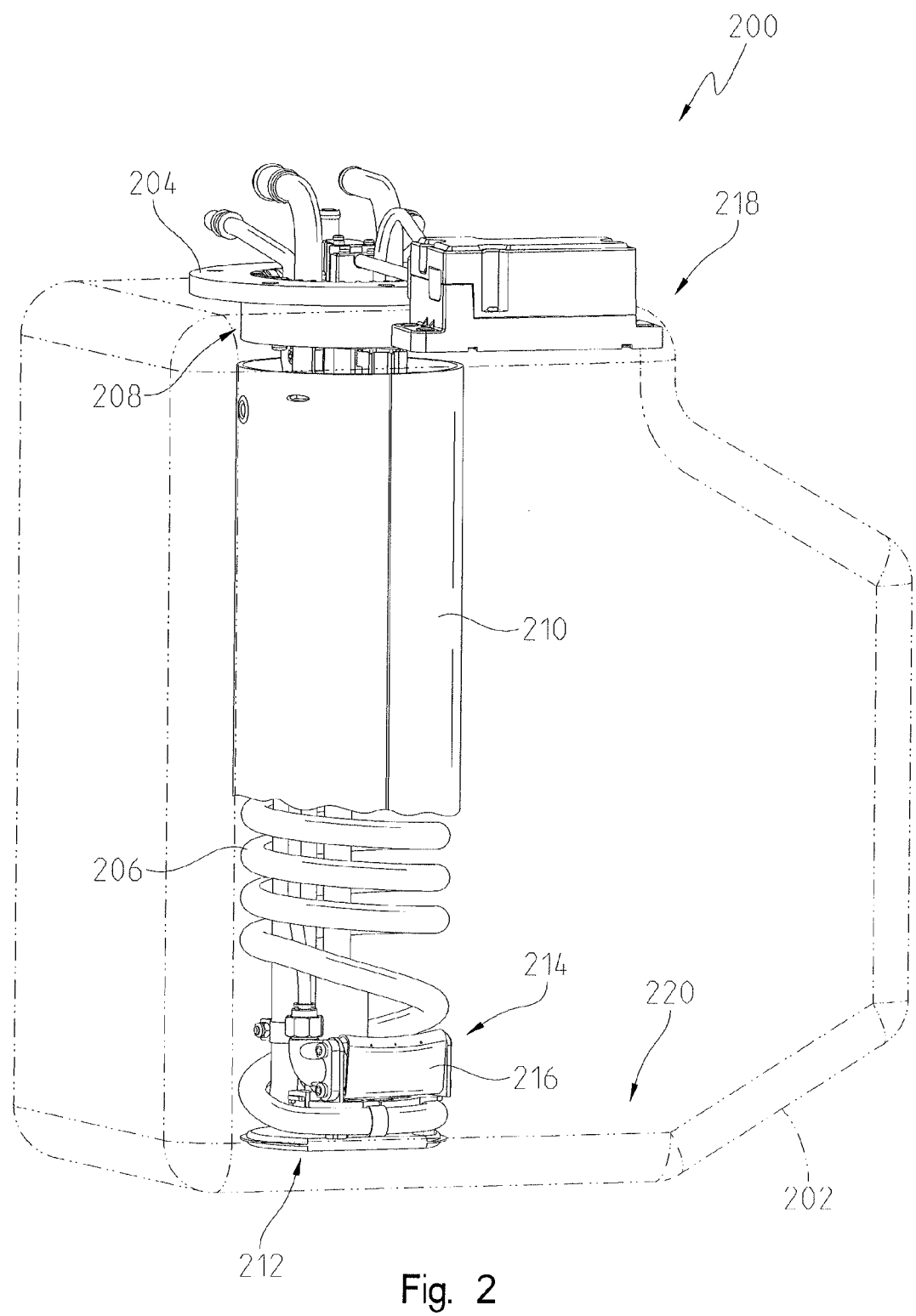
FIG. 2 is a partial perspective view of the diesel exhaust fluid tank of FIG. 1 and a sensor assembly.

Referring to FIG. 2, a tank assembly 200 such as the DEF tank 116 is illustrated. The tank assembly 200 may include a tank housing 202 for containing a fluid such as water and DEF. The tank housing 202 may include a top end 218 and a bottom end 220. The tank housing 202 may include one or more walls that define an inner chamber for holding the DEF. At least at its top end 218, the tank housing 202 may include an opening through which a header assembly 208 is disposed. The header assembly 208 may be coupled to the tank housing 202 according to any known method. The header assembly 208 may extend into the inner chamber of the housing 202. As shown in FIG. 2, a bottom portion of the header assembly 208 may include a filter 212 that is in contact or close proximity with the bottom end 220 of the tank housing 202.

The header assembly 208 may include a header 204 and one or more coils of coolant lines 206 that wind around the header 204. The coolant lines 206 may contain a fluid for thawing the DEF inside the tank housing 202 when it freezes. Since DEF may freeze at or near −11° C., the coolant lines may be operably disposed to thaw the DEF.

As mentioned above with reference to FIG. 1, a plurality of sensors may be coupled to the header assembly. In FIG. 2, a sensory assembly 214 for detecting a concentration or quality of the DEF in the tank housing 202 is provided. The sensor assembly 214 may be coupled to the header 204. The sensor assembly 214 may include a sensor or sensing unit for detecting a fluid concentration, and a cover assembly 216 may be further provided to completely or partially enclose the sensor or sensor unit. As shown, the sensor assembly 214 may be coupled to the header 204 at a location proximate the bottom end or portion of the tank housing 202. With this placement, the sensor assembly 214 may detect fluid concentration even when the fluid level inside the tank is low or getting low.

In addition to the sensor assembly 214, a baffle 210 is shown surrounding or enclosing the sensor assembly 214. The baffle 210 may completely or partially encapsulate the coolant lines 206 and sensor assembly 214. As such, the baffle 210 offers structural protection to the sensor assembly as will be describe below.

Figure 3:
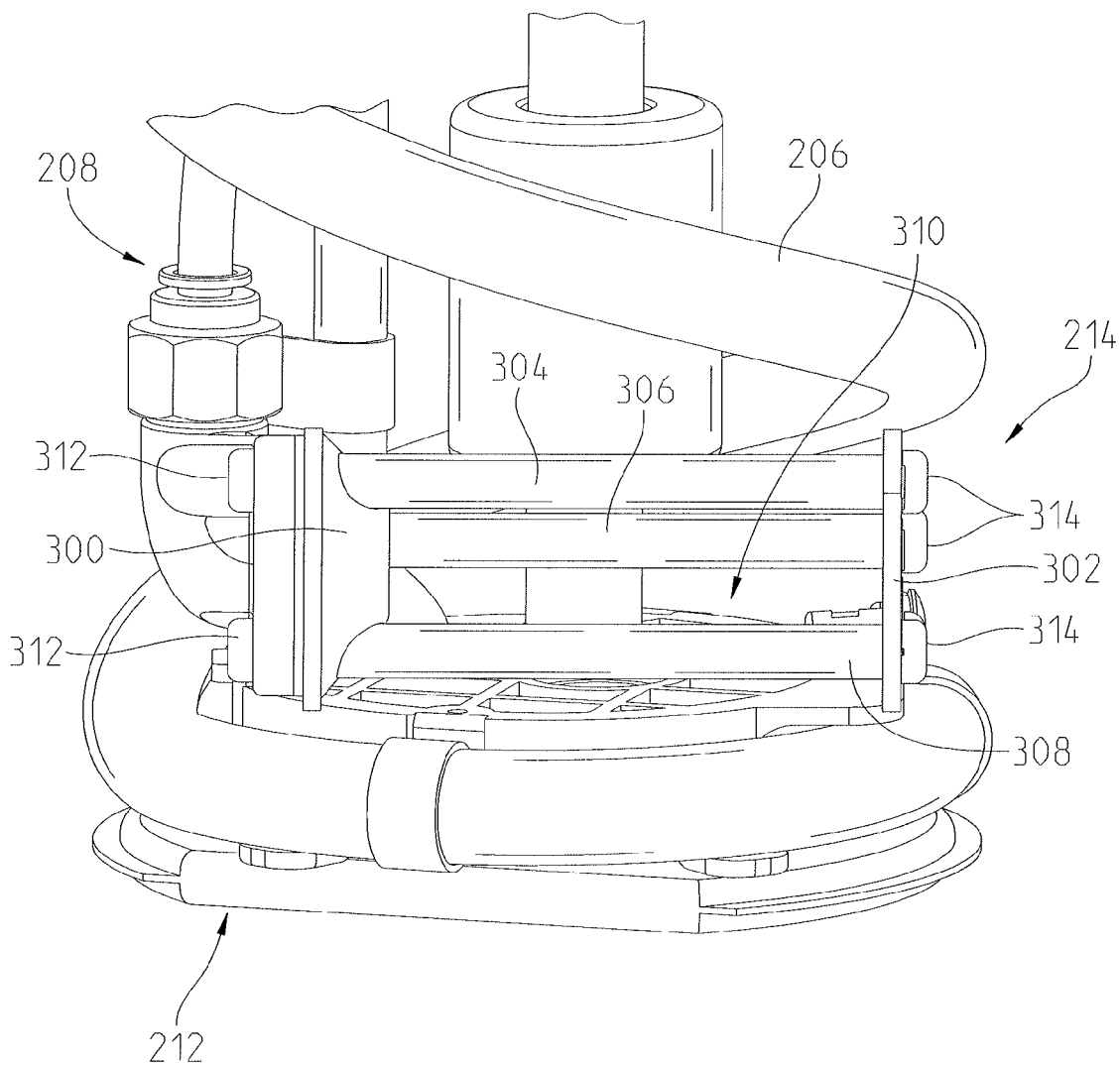
FIG. 3 is a partial perspective view of the sensor assembly of FIG. 2 with its cover assembly removed.

As described above, one of the issues affecting sensors that are coupled to the header assembly 208 or are otherwise disposed within the tank housing 202 is when the fluid contained within the tank begins to splash or slosh around. This can often produce air or gaseous bubbles within the fluid. Turning to FIG. 3, for example, the sensor assembly 214 may be in the form of an ultrasonic transducer capable of transmitting sonic waves through the fluid. The assembly 214 may include a transmitter 300 or piezo plate coupled to the header assembly 208 via one or more fasteners 312. The transmitter 300 may transmit a signal through the fluid and which is received by a receiver 302 or reflector plate. As shown, the transmitter 300 and receiver 302 may be axially aligned with and offset from one another. A plurality of support bars may be coupled between the two plates including a first support bar 304, a second support bar 306, and a third support bar 308. In this embodiment, each of the support bars is parallel to and spaced from one another. Each support bar may be formed of stainless steel and maintains its orientation of perpendicularity with respect to the transmitter 300 and receiver 302. Fasteners 312 may further couple the support bars to the transmitter 300, whereas fasteners 314 may couple the support bars to the receiver 302.

An area defined between the transmitter 300 and receiver 302 and each of the support bars may be referred to as a sensing volume 310. During operation, the transmitter 300 may send a sonic wave or signal through at least a portion of the sensing volume 310 to the receiver 302. The amount of time the signal travels through the sensing volume 310 may be used by the sensor assembly 214 to detect a concentration or quality of the fluid. Although not shown, the sensor assembly 214 may be in electrical communication with a controller or other control unit to communicate the fluid concentration. In a vehicle or machine, an engine control unit (ECU) or vehicle controller may receive the fluid concentration and make further determinations about the fluid. For instance, the controller may compare the detected fluid concentration to a threshold value, and based on the comparison, the controller may determine the fluid quality is satisfactory or needs servicing. If the DEF concentration is of poor quality, the controller may alert the driver of the vehicle or machine regarding the fluid quality and communicate the need for servicing the engine or fluid.

In the event air bubbles or the like form inside the tank, these gases may introduce error in the detection of the fluid concentration. For example, if a gaseous portion of the fluid passes through the sensing volume 310, the signal from the transmitter to the receiver may be interfered with or otherwise affected by the gaseous portion. As a result, the fluid concentration may not be accurately detected. To overcome or reduce the impact of air or gas bubbles forming in the fluid and negatively affecting sensor function, several structural designs have been incorporated into the tank assembly 200 of FIG. 2 and the sensor assembly 214 as will be described.

For one, the added media baffle 210 is disposed around and substantially encloses the sensor assembly 214 and sensing volume 310. The baffle 210 may be formed of an impermeable material such as a plastic or polymer. In one example, the baffle 210 may be formed of a polypropylene material. Other materials may be possible as well such as stainless steel or other DEF-compatible material. In effect, air bubbles that form between the baffle 210 and the tank housing 202 are precluded from permeating into the sensing volume 310. The baffle 210 may completely surround the header assembly 208 and extend from the top portion 218 of the tank assembly 200 to the bottom portion 220 thereof. Although not shown, the baffle 210 may be at least partially enclosed on its upper and lower ends to prevent air bubbles from entering the sensing volume 310.

In addition to the baffle, the sensor assembly 214 has been designed to include an outer cover assembly 216. The cover assembly 216 may be formed of one or more pieces to at least partially enclose the sensing volume 310. As such, the sensing volume 310 may be at least partially enclosed by both the baffle 210 and the cover assembly 216.

The cover assembly 216 may be formed of different materials which are impermeable and non-corrosive. Moreover, the cover assembly 216 may be formed of a material that is compatible with DEF. This may include a plastic or polymer material, or in some cases, a stainless steel. The cover assembly 216 may be formed of other known impermeable materials as well. If used in a DEF tank, the cover assembly 216 may be formed of a material durable enough to withstand freezing and thawing of the DEF. A surface finish on an interior wall of the cover assembly 216 may be formed with a certain roughness that can absorb rather than reflect the sonic waves passing through the sensing volume. In at least one non-limiting example, it may be desirable to produce a non-smooth surface finish on the interior wall of the cover assembly 216 for this reason.

In a conventional after treatment system, a suction line and return line may be connected to the DEF tank. A pump may be connected to the suction line at a location external to the tank, and the pump may pressurize the overall system. The return line is provided to return fluid to the tank and air or other gaseous bubbles can form in the return line. DEF is often more prone to aeration than water, and thus these bubbles can form in the return line. In the embodiment of FIG. 2, the return line may be fluidly coupled to the tank housing 202 at a location outside of the baffle 210. Thus, the baffle 210 can prevent or reduce air bubbles from entering the sensing volume 310.

With that said, however, the splashing or sloshing of DEF inside the baffle can still produce air or gaseous bubbles. The cover assembly 216 can often prevent or reduce the number of air bubbles from forming or entering the sensing volume 310. Air or other gaseous bubbles, however, may still form inside the cover assembly 216 even without splashing or sloshing, and thus the cover assembly 216 may be designed to allow these bubbles to escape as needed. As such, while the cover assembly 216 may be formed of an impermeable material, the cover assembly 216 may include at least one portion of which is permeable.

Figure 4:
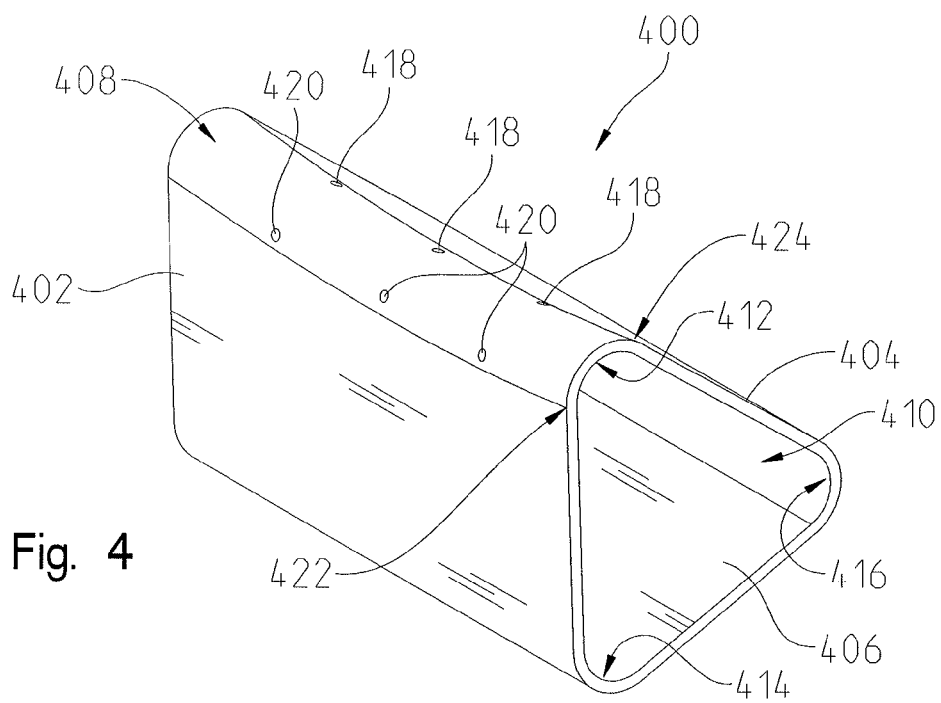
FIG. 4 is a perspective view of one embodiment of a cover assembly.

Referring to FIG. 4, for example, one embodiment of a cover assembly 400 is shown. The cover assembly 400 may include a first side 402, a second side 404, and a third or bottom side 406. The first side 402 and second side 404 may be coupled to one another and form top side or surface 408. For purposes of this disclosure, the top surface 408 is considered the surface or side of the cover assembly that is oriented in a direction towards the top end or portion 218 of the tank assembly 200. In some embodiments, the cover assembly 400 may be at least partially open on its bottom end. For example, the bottom side 406 may be removed or formed with a large opening therein. The bottom side 406 may be optional in certain embodiments. In the illustrated embodiment of FIG. 4, however, the cover assembly 400 is a continuous structure inclusive of the different sides.

The different sides of the cover assembly 400 defines an interior 410. The sensor and sensing volume 310 may be positioned within the interior 410 of the cover assembly 400. As such, the cover assembly 400 at least partially encloses or surrounds the sensing volume 310. Moreover, the size and shape of the cover assembly 400 may depend upon the size and shape of the sensor (e.g., in FIG. 3, the size and shape of the transmitter 300 and receiver 302). In FIG. 4, the cover assembly 400 has a triangular cross-section. In other examples, the cover assembly may have a square, circular, oval, rectangular, or polygonal cross-section. In FIG. 3, the sensor assembly 214 includes three support bars disposed between the transmitter 300 and receiver 302. In this embodiment, the cover assembly may be triangular as shown in FIG. 4. Thus, in one non-limiting example, the number of support bars may correspond with the number of sides and cross-section of the cover assembly. However, in another embodiment, the cover assembly may be substantially cylindrical regardless of the number of support bars. Alternatively, the shape of the cover assembly may correspond with the shape of the transmitter or receiver. This may not be the case in other embodiments.

Figure 6:
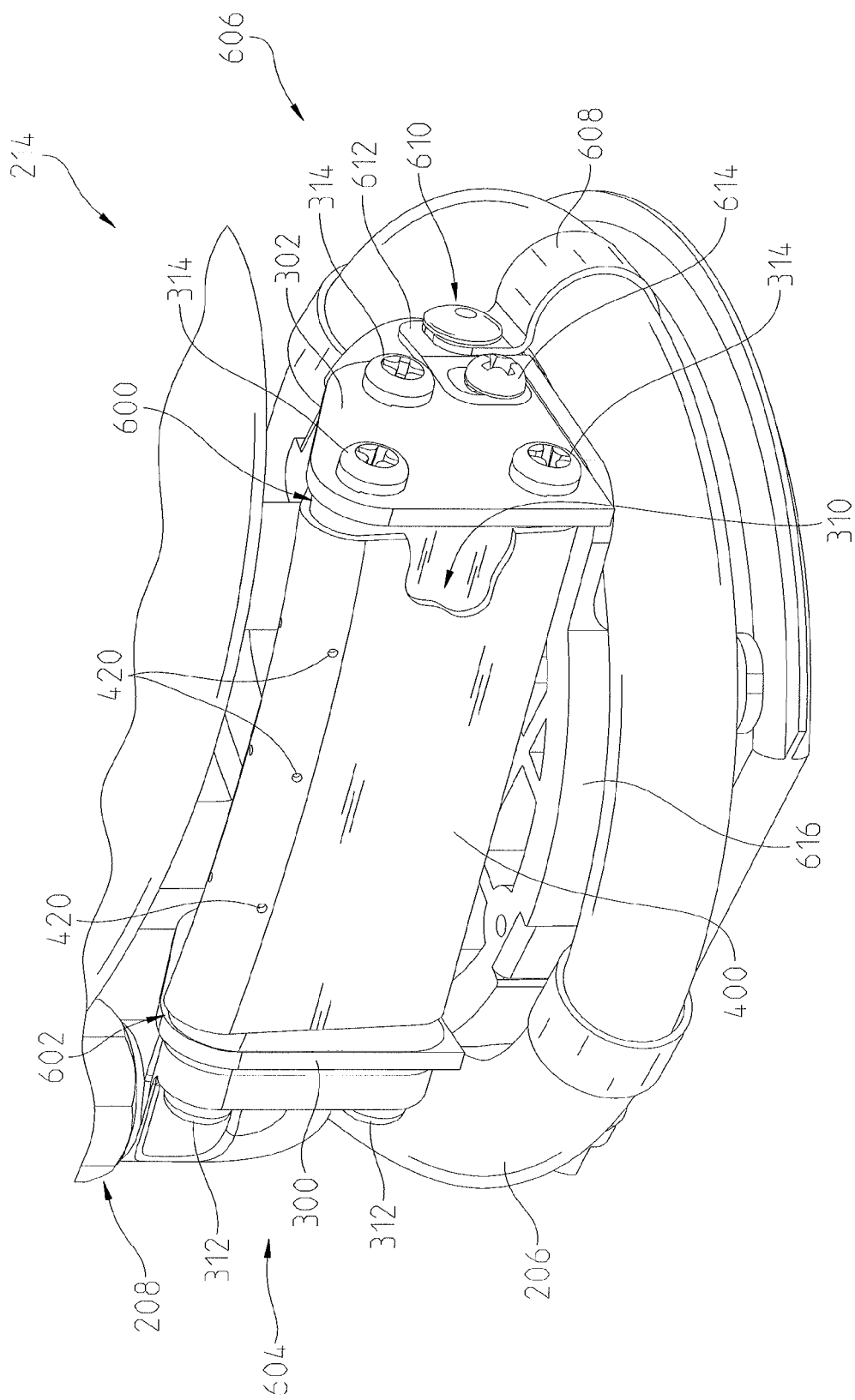
FIG. 6 is a partial perspective view of the sensor assembly of FIG. 2 with the cover assembly of FIG. 4.

The cover assembly 400 may be coupled to the header assembly 208, transmitter 300, receiver 302 or one or more of the support bars. In another embodiment, however, the cover assembly 400 may float relative to the rest of the sensor, i.e., it is not coupled to any of the aforementioned structures. In FIG. 6, however, an embodiment is illustrated in which the cover assembly 400 may be coupled to a support block or the like at a location below the sensor assembly 214. Thus, the arrangement of how the cover assembly is coupled or not to the rest of the sensor may vary based on the type of embodiment, and in any event, the cover assembly 400 may be coupled to or float relative to the sensor such that it does not impact the function of the sensor.

The cover assembly 400 may further include one or more openings or apertures defined therein. In FIG. 4, for example, a first set of apertures 418 and a second set of apertures 420 are shown. Each set of apertures may be formed in or near the top side or surface 408. These apertures form a permeable portion of the cover assembly 400 such that air or other gaseous bubbles may escape from the interior 410 thereof. Each aperture may be spaced equidistantly from an adjacent aperture along a longitudinal direction of the cover assembly 400. Moreover, the apertures may be positioned in the cover assembly 400 at a location where the air bubbles may aggregate or form over time. In FIG. 4, for example, this is shown as being towards the top of the cover assembly 400. In other embodiments, however, the location of these apertures may differ, and may be located at one side of the cover assembly.

As shown in FIG. 4, the cover assembly 400 includes a plurality of curved edges. For example, a first curved edge 412 is formed at the adjoining location of the first and second sides. A second curved edge 414 is formed at the adjoining location of the first side 402 and the third side 406. Likewise, a third curved edge 416 may be formed at the adjoining location of the second side 404 and third side 406. In each location, the respective curved edge may define a radial or arc-shaped edge. In FIG. 4, the first curved edge 412 defines a first arc end 422 and a second arc end 424. Depending upon the orientation of the cover assembly 400 with respect to the sensor, the first arc end 422 may be positioned at the highest point of the cover assembly. Alternatively, the second arc end 424 may be positioned at the highest location within the tank. In a further example, a point along the curved edge between the two arc ends may be at the highest location of the cover assembly 400 within the tank. This highest location may define a local maxima of where air bubbles aggregate within the interior 410 of the cover assembly 400. It is at this location that some or all of the apertures may be positioned within the cover assembly 400.

Figure 5:
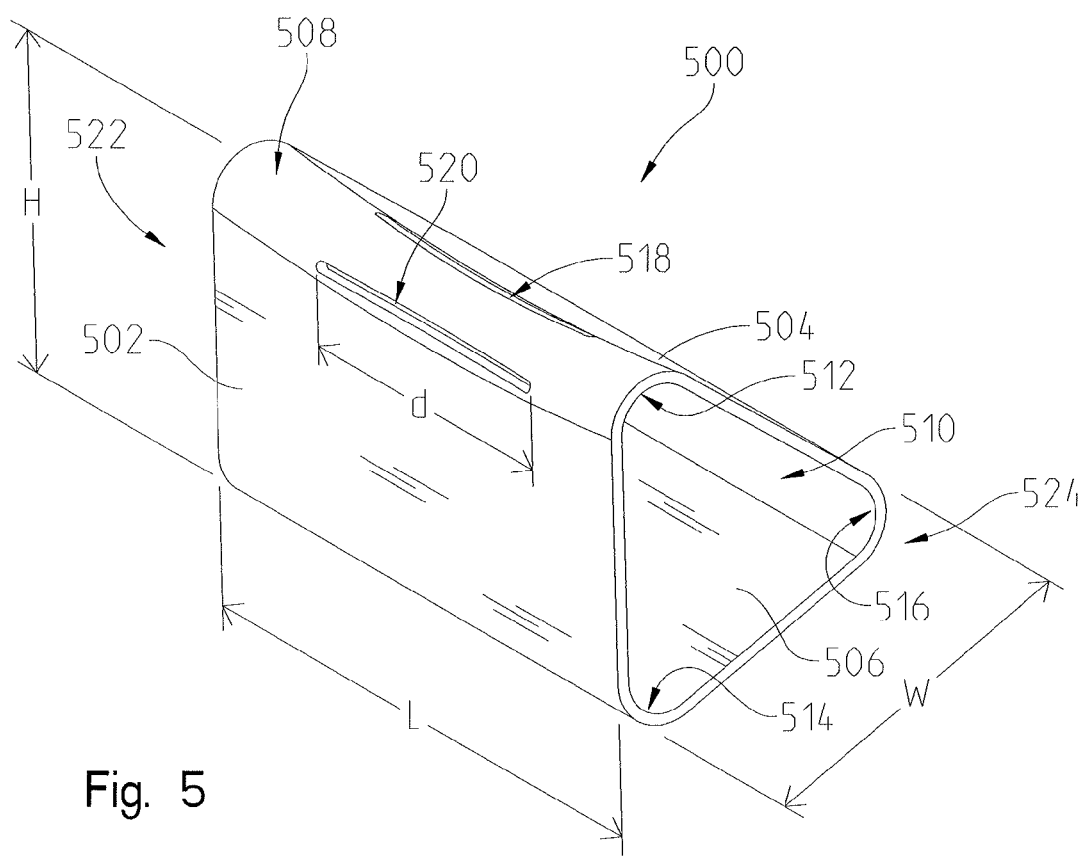
FIG. 5 is a perspective view of a second embodiment of a cover assembly.

Referring to FIG. 5, another embodiment of a cover assembly 500 is shown. Here, the cover assembly 500 is similarly shaped as the cover assembly 400 of FIG. 4. The cover assembly 500 may include a plurality of sides including a first side 502, a second side 504, and a third side 506. Each side defines an interior 510 of the cover assembly 500 in which the sensing volume 310 may be disposed. Each side may be dimensioned the same, or alternatively, each side may have a different length, width, and thickness. In FIG. 5, the cover assembly 500 includes a length, L, a width, W, and a height, H. The different sides of the cover assembly 500 may also define a first curved edge 512, a second curved edge 514, and a third curved edge 516. In other embodiments, one or more of these edges may be substantially straight, i.e., not curved.

The first side 502 and the second side 504 may be coupled to one another at or near a top side or surface 508. This top surface may have a width to it that is less than the width of one of the sides (W). The top surface 508 may also have a length that is the same as the overall length L of the cover assembly 500. In other embodiments, however, the shape of the cover assembly 500 may be such that the length or width of the top surface varies or is different from that shown in FIG. 5.

The cover assembly 500 of FIG. 5 may further include one or more openings or apertures defined therein. These openings are formed as one or more longitudinal slots defined in the cover assembly 500. Here, a first slot 518 and a second slot 520 are shown. Each slot has a defined length "d" which is less than the overall length L of the cover assembly 500. Each slot forms part of the permeable portion of the cover assembly 500 to allow air and other gaseous bubbles to escape from the sensing volume 310.

The first and second slot may be positioned within the cover assembly 500 at a location where the air bubbles likely aggregate. In other words, in FIG. 5, the slots are defined in or near the top side or surface 508 of the cover assembly 500. While only two slots are shown, there may be any number of slots from one or more. A larger cover assembly may require more slots, whereas a smaller cover assembly may only need a single slot.

In FIG. 5, each of the first and second slot are oriented or positioned within the cover assembly 500 such that each is substantially parallel with the support bars of the sensor. In some embodiments, however, one or more of the slots may be disposed in a position which is not parallel to the support bars. In other embodiments regardless of the type of sensor, the slots may be desirably oriented to allow the maximum number of air bubbles to escape from the sensing volume 310.

Moreover, the slots may be positioned equidistant from each end of the cover assembly 500. For instance, the cover assembly 500 may include a first end 522 and a second end 524. The first slot 518 and the second slot 520 may be formed in the cover assembly 500 at the same distance from each end. In other embodiments, however, the slots may be positioned closer to the transmitter 300, whereas in other embodiments the slots may be positioned closer to the receiver 302.

Referring to FIG. 6, the cover assembly 400 of FIG. 4 is shown at least partially encapsulating or enclosing the sensor and sensing volume 310. As shown, the cover assembly 400 may be positioned relative to the sensor such that a first end gap 600 and a second end gap 602 are formed. The first end gap 600 may be formed between a first end 604 of the cover assembly 400 and the transmitter 300, and the second end gap 602 may be formed between a second end 606 and the receiver 302. In one non-limiting example, at least one gap may be at least 1 mm wide. In another non-limiting example, at least one gap may be between 1-2 mm. In another example, at least one gap may be greater than 2 mm.

Each gap may be larger if the cover assembly 400 includes a curved edge between adjacent sides, such as shown in FIGS. 4 and 5. In any event, the combination of the plurality of apertures and gaps allows air or gaseous bubbles to escape from the sensing volume 310 and to a location external of the cover assembly. While the baffle 210 and cover assembly operably limit or prevent air or other gaseous bubbles from entering the sensing volume 310, neither may be able to prevent microbubbles from forming inside or entering the sensing volume. The cover assembly, however, includes a permeable portion in the form of the apertures, slots or gaps to allow these bubbles to escape from the sensing volume and not negatively affect the detection capability of the sensor assembly 214.

Although not shown in great detail, the location of the slots or apertures of the cover assembly may be positioned such that the support bars of the sensor do not partially or complete block bubbles from escaping the sensing volume 310. As such, the cover assembly may be positioned relative to the sensor such that the slots or apertures are spaced from each of the plurality of support bars of the sensor. In other embodiments where the sensor does not include support bars, the cover assembly is desirably positioned such that there is no structure that partially or completely covers or obstructs the slots or apertures.

As also shown in FIG. 6, the cover assembly 400 may float relative to the sensor but is coupled to the support block 616, as previously described. The transmitter 300 may be coupled to the header assembly 208, and the receiver 302 may be coupled to one of the coolant lines 206. As shown, a connector 608 may be fastened to the coolant line 206 and a rivet 610 or the like may connect the connector 608 to a bracket 612. The bracket 612 may be coupled to the receiver 302 via one or more fasteners 614.

In another embodiment of the present disclosure, the cover assembly may form an open frame that is at least partially wrapped or covered with a plastic material. One example may include a polypropylene fiber material similar to that of the baffle 210. In this manner, the cover assembly may completely enclose the sensing volume. Further, the cover assembly may be mechanically fastened to the header assembly.

In a different embodiment, the cover assembly may be formed of a mesh material. In a further embodiment, the cover assembly may form a continuous structure that substantially encloses the sensing volume except at each end where the receiver and transmitter are located. Alternatively, the cover assembly may be a discontinuous structure where the cover assembly is open at one side. This may be a bottom side, but it is not limited to such. In another example, the cover assembly may include large openings or holes formed in one of the sides to allow bubbles to escape.

In yet a further embodiment, the cover assembly may be enclosed at one end such that the enclosed end forms the receiver. In this manner, a transmitter may be coupled to the header assembly 208 and the cover assembly may be positioned relative to the transmitter so that signals may be transmitted through a sensing volume and received at the enclosed end of the cover assembly.

In a different embodiment, the cover assembly may be enclosed at one end and the enclosed end may include a signal transmitter. In this embodiment, the header assembly may include a receiver for receiving a transmitted signal.

While ultrasonic signals have been described in this disclosure, other types of sensors and transmitted signals are contemplated herein. For example, an electrical signal may be transmitted or otherwise used to detect fluid concentration. The skilled artisan can appreciate other known sensors and types of signals that may be used.

The cover assembly may comprise any size, shape and material that includes at least a permeable portion and an impermeable portion. The size and shape of the cover assembly may permit a limited amount of aeration from within an enclosed or partially enclosed sensing volume, but it limits excessive aerated fluid from entering the sensing volume. Openings such as apertures or slots defined in the cover assembly, along with gaps defines at the edges of the cover assembly, achieve this partial aeration. As such, the fluid sensing element and sensing volume is protected from static air bubbles and other aeration formed by splashing or sloshing of fluid inside the tank assembly.

While embodiments incorporating the principles of the present disclosure have been described hereinabove, the present disclosure is not limited to the described embodiments. Instead, this application is intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A sensor assembly for detecting a concentration of a fluid, comprising:
   a sensing unit including a transmitter configured to transmit a signal into a sensing volume and a receiver configured to receive the signal after the signal passes through a portion of the sensing volume;
   a cover assembly at least partially enclosing the sensing volume and being substantially impermeable to a gas portion of the fluid, the cover assembly including apertures defined therein which are permeable to the gas portion of the fluid;
   wherein, a first plurality of apertures are defined along a top surface of the cover assembly;
   wherein, the cover assembly includes a first open end and a second open end, the transmitter disposed at the first open end and the receiver disposed at the second open end.

2. The sensor assembly of claim 1, wherein the signal is sonic.

3. The sensor assembly of claim 1, wherein:
   the cover assembly comprises a bottom surface; and
   a second plurality of apertures are defined in the bottom surface.

4. The sensor assembly of claim 1, wherein the top surface comprises a curved cross-section forming an arc, the arc having a first end and a second end, where the top surface defines an uppermost portion positioned at a location at or between the first and second ends of the arc.

5. The sensor assembly of claim 1, wherein the apertures are positioned at a location in the cover assembly nearest the transmitter.

6. The sensor assembly of claim 1, wherein the apertures are positioned at a location in the cover assembly nearest the receiver.

7. The sensor assembly of claim 1, wherein the cover assembly is oriented with respect to the sensing unit and sensing volume such that the first plurality of apertures are positioned at or near a location in the top surface of the cover assembly where the gas portion of the fluid aggregates.

8. A sensor assembly for detecting a quality of fluid inside a diesel exhaust fluid tank assembly, comprising:
a sensor including a first plate for transmitting a sonic signal through a sensing volume, a second plate spaced from the first plate for receiving the sonic signal as the sonic signal passes through at least a portion of the sensing volume, and a plurality of support members spaced from one another and coupled between the first and second plates;
a cover assembly including an outer wall at least partially enclosing the sensor, the cover assembly being impermeable to a gas portion of the fluid except for openings defined in the outer wall of the cover assembly which are permeable to the gas portion of the fluid to allow the gas portion to escape from the sensing volume therethrough;
a baffle disposed around the cover assembly and sensor, wherein, a first plurality of openings is defined in a top portion of the outer wall of the cover assembly;
further wherein, a first space is defined between the cover assembly and the first plate and a second space is defined between the cover assembly and the second plate, the first space and the second space being permeable to the gas portion of the fluid.

9. The sensor assembly of claim 8, wherein the cover assembly floats relative to the sensor.

10. The sensor assembly of claim 8, wherein a bottom portion of the outer wall of the cover assembly is open and does not enclose the sensing volume.

11. The sensor assembly of claim 8, wherein the cover assembly is coupled to the first plate, the second plate or one of the plurality of support members.

12. The sensor assembly of claim 8, wherein the first plurality of openings comprises one or more longitudinal slots defined in the top portion of the outer wall.

13. The sensor assembly of claim 12, wherein:
the one or more longitudinal slots are substantially parallel to the plurality of support members; and
each of the one or more longitudinal slots is defined in the cover assembly at a location spaced from each of the plurality of support members.

14. The sensor assembly of claim 8, wherein the outer wall of the cover assembly forms a first curvature and a second curvature, the first curvature positioned at the first space and the second curvature positioned at the second space.

15. The sensor assembly of claim 8, wherein:
the outer wall of the cover assembly comprises a first side wall, a second side wall, a top wall, and a bottom wall, the bottom wall coupled to the first side wall and the second side wall; and
the top wall, bottom wall, first side wall, and second side wall form a continuous structure that substantially surrounds the sensor.

16. The sensor assembly of claim 8, wherein:
the baffle is defined about a first axis passing therethrough; and
the cover is defined about a second axis passing therethrough;
further wherein, the first axis is perpendicular to the second axis.

17. A diesel exhaust fluid tank assembly for containing a fluid, comprising:
a tank defining an interior cavity for holding diesel exhaust fluid;
a header assembly coupled to the tank, the header assembly including a fluid level sensor and a temperature sensor coupled thereto;
a sensor disposed in the interior cavity of the tank, the sensor including a first plate for transmitting a sonic signal through a sensing volume, a second plate spaced from the first plate for receiving the sonic signal after it passes through at least a portion of the sensing volume, and a plurality of support members spaced from one another and coupled between the first and second plates, wherein the first plate is coupled to the header assembly;
a cover assembly at least partially enclosing the sensing volume, the cover assembly including a top wall, a first side wall, and a second side wall, the cover assembly being open at both ends such that a first space is defined between the cover assembly and the first plate and a second space is defined between the cover assembly and the second plate; and
a baffle coupled to the header assembly and enclosing the cover assembly and sensor;
wherein, the cover assembly is impermeable to a gas portion of the fluid except for openings defined in the cover assembly and the first and second spaces which are permeable to the gas portion.

18. The tank assembly of claim 16, wherein the cover assembly comprises a first plurality of openings defined in or near the top wall to allow the gas portion of the fluid to escape from the sensing volume through the cover assembly.

19. The tank assembly of claim 18, wherein:
the first plurality of openings comprises one or more longitudinal slots;
the one or more longitudinal slots are substantially parallel to the plurality of support members; and
each of the one or more longitudinal slots is defined in the cover assembly at a location spaced from each of the plurality of support members.

20. The tank assembly of claim 16, wherein the first plurality of openings are equally spaced from one another and the first and second spaces.

* * * * *